（12） United States Patent
Bezanson et al.

(10) Patent No.: US 8,231,921 B2
(45) Date of Patent: Jul. 31, 2012

(54) HIGH PERFORMANCE GELLAN GUMS AND METHODS FOR PRODUCTION THEREOF

(75) Inventors: Ralph B. Bezanson, Alpine, CA (US); William C. Baldwin, San Diego, CA (US); Daniel E. Jackson, San Diego, CA (US); Bradley S. Dominik, San Diego, CA (US); Don Dimasi, San Diego, CA (US); C. Ronnie Yuan, San Diego, CA (US); Andrew J. Grazela, San Diego, CA (US)

(73) Assignee: CP Kelco U.S., Inc.

( * ) Notice: Subject to any disclaimer, the term of this patent is extended or adjusted under 35 U.S.C. 154(b) by 1360 days.

(21) Appl. No.: 11/611,570

(22) Filed: Dec. 15, 2006

(65) Prior Publication Data

US 2008/0145505 A1  Jun. 19, 2008

(51) Int. Cl.
*A23L 1/05* (2006.01)
(52) U.S. Cl. ...................................... 426/576
(58) Field of Classification Search .................... 426/49, 426/576
See application file for complete search history.

(56) References Cited

U.S. PATENT DOCUMENTS

| | | | |
|---|---|---|---|
| 4,119,491 A * | 10/1978 | Wellington | .................... 435/274 |
| 4,503,084 A | 3/1985 | Baird et al. | |
| 5,190,927 A | 3/1993 | Chang et al. | |
| 5,300,429 A | 4/1994 | Baird et al. | |
| 6,586,213 B2 * | 7/2003 | Kobzeff et al. | ............... 435/104 |
| 6,663,911 B2 | 12/2003 | Valli et al. | |
| 2003/0100078 A1 | 5/2003 | Harding et al. | |
| 2008/0268527 A1 * | 10/2008 | Bower et al. | ................... 435/274 |

OTHER PUBLICATIONS

PCT/US2007/087111 International Search Report and Written Opinion.
European Search Report for European Patent Application No. 07869117.7 dated Apr. 16, 2010.
International Search Report and Written Opinion for International application No. PCT/US07/87111 dated Aug. 26, 2008.
International Search Report and Written Opinion for International application No. PCT/US07/87111 dated Aug. 22, 2008.
International Preliminary Report on Patentability for PCT/US07/087111, International Searching Authority, mailed Jun. 16, 2009.

* cited by examiner

*Primary Examiner* — D. Lawrence Tarazano
*Assistant Examiner* — Katherine DeGuire
(74) *Attorney, Agent, or Firm* — Sutherland Asbill & Brennan LLP

(57) ABSTRACT

The invention relates to high performance gellan gum compositions having a 0.1% curdmeter gel strength of at least about 117 g/cm$^2$, i.e. from about 117 g/cm$^2$ to about 400 g/cm$^2$. The high performance gellan gums have a low acyl content but an increased molecular weight. One embodiment of the invention also relates to processes for producing high performance gellan gums having high clarity. The invention further relates to food and non-food industrial products comprising high performance gellan gums.

50 Claims, 1 Drawing Sheet

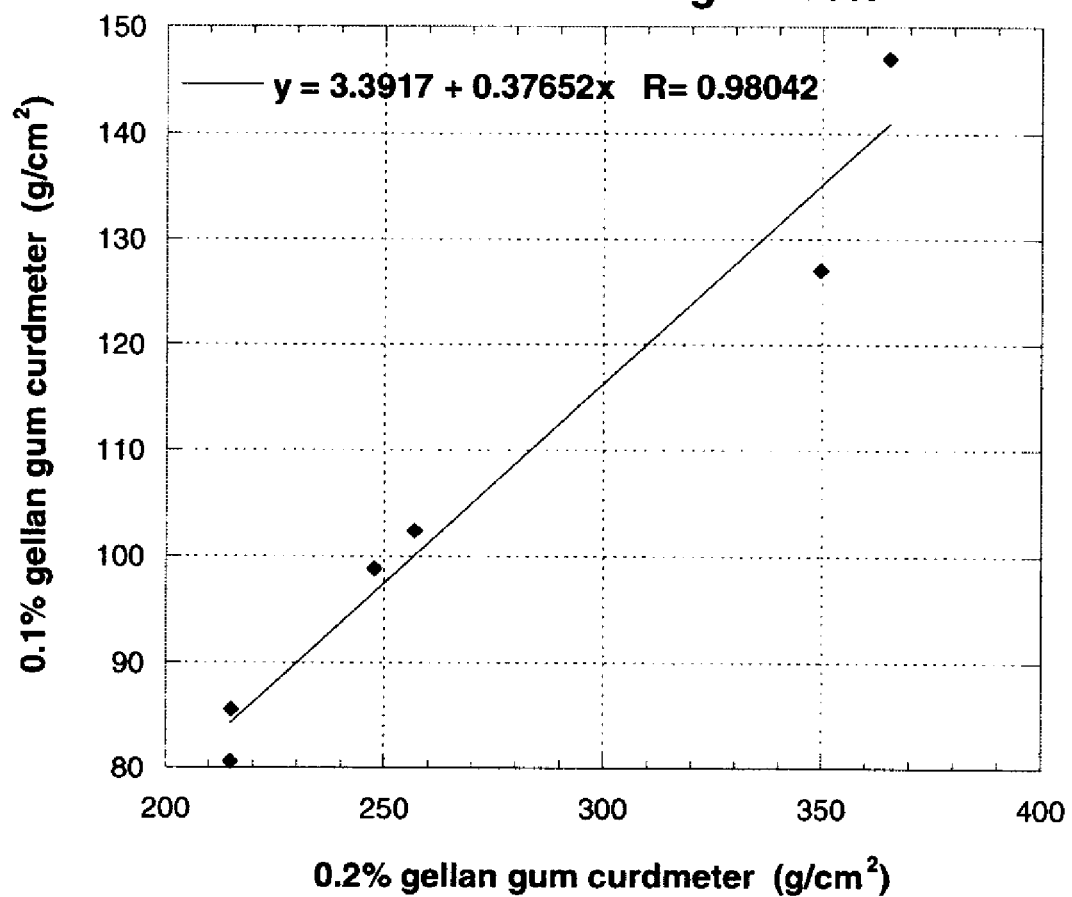

HIGH PERFORMANCE GELLAN GUMS AND METHODS FOR PRODUCTION THEREOF

BACKGROUND OF THE INVENTION

1. Field of the Invention

The invention relates to high performance low acyl and partially deacylated gellan gum compositions having increased molecular weight and increased gel strength. The invention also relates to processes for producing high performance low acyl and partially deacylated gellan gums having high clarity without using the conventional filtration process. The invention further relates to industrial products comprising high performance low acyl and partially deacylated gellan gums for food and non-food applications.

2. Description of Related Art

Polysaccharides, which are also referred to as gums, are primarily used to thicken or gel aqueous solutions. Polysaccharides that are produced by microorganisms of the genus *Sphingomonas* are also referred to as sphingans. Gums are frequently classified into two groups: thickeners and gelling agents. Typical thickeners include starches, guar gum, carboxymethylcellulose, alginate, methylcellulose, xanthan gum, gum karaya, and gum tragacanth. Common gelling agents include gellan gum, gelatin, starch, alginate, pectin, carrageenan, agar, and methylcellulose.

Gelling agents are used in the food industry in a variety of applications, including confectionery jellies, jams, dessert gels, icings, dairy products, beverages, and the like. Additionally, gelling agents may be used as components of microbiological media. Gelling agents differ in the conditions under which they may be used and in the texture of the gels they form. These distinctive properties of gels have led to the widespread use of certain gelling agents in particular products (e.g., starch in confectionery jellies; gelatin in dessert gels; agar in icings; and alginate in pimento strips).

One particularly useful gelling agent is gellan gum, which is a capsular polysaccharide produced by the bacterium *Sphingomonas elodea*, ATCC 31461, and strains derived from this species. The constituent sugars of gellan gum are glucose, glucuronic acid and rhamnose in the molar ratio of 2:1:1. These are linked together to give a primary structure comprising a linear tetrasaccharide repeat unit (O'Neill M. A., et al., Structure of the acidic extracellular gelling polysaccharide produced by *Pseudomonas elodea*, Carbohydrate Res., 124(1):123-133 (1983); Jansson, P. E., et al., Structural studies of gellan gum, an extracellular polysaccharide elaborated by *Pseudomonas elodea*, Carbohydrate Res., 124(1):135-139 (1983)). In the native or high acyl ("HA") form, two acyl substituents, acetate and glycerate, are present. Both substituents are located on the same glucose residue and, on average, there is one glycerate per repeat unit and one acetate per every two repeat units. In the low acyl ("LA") form, most of the acyl groups have been removed to produce a linear repeat unit substantially lacking such groups. X-ray diffraction analysis shows that gellan gum exists as a three-fold, left-handed, parallel double helix (Chandraskaran, R., et al., The crystal structure of gellan, Carbohydrate Res., 175(11):1-15 (1988); Chandraskaran, R., et al., Cation interactions in gellan: An x-ray study of the potassium salt, Carbohydrate Res., 181:23-40 (1988)).

LA gellan gums form gels when cooled in the presence of gel-promoting cations, preferably divalent cations, such as calcium and magnesium. The gels formed are firm and brittle. HA gellan gums do not require the presence of cations for gel formation and the gels formed have structural and rheological characteristics which are significantly affected by the acyl substituents. Thus the properties of HA gellan gums differ significantly from those of LA gellan gums. HA gellan gum gels are typically soft and flexible and lack thermal hysteresis.

Commercially, gellan gum is formed by inoculating a fermentation medium under aerobic conditions with *Sphingomonas elodea* bacteria. The fermentation medium contains a carbon source, phosphate, organic and inorganic nitrogen sources, and appropriate trace elements. The fermentation is conducted under sterile conditions with strict control of aeration, agitation, temperature, and pH. Upon completion of the fermentation, the viscous broth is pasteurized to kill viable cells prior to recovery of the gum.

Gellan gum displays different characteristics depending upon the method of recovery from the fermentation broth. Direct recovery from the fermentation broth yields gellan in its native or high-acyl form, which is modified by *S. elodea* with acetyl and glyceryl substituents on one glucose residue. Isolation of gellan in this native or high-acyl form yields a soft, flexible, elastic gel. Gellan may be deacylated to provide gellan in its low acyl form. Isolation of gellan in this low acyl form yields a hard, firm, brittle gel. Blends of native and low acyl gellan produce gels of intermediate texture.

Currently, gellan gum is deacylated by treating the fermentation broth containing the gellan gum with strong alkali at high temperature. This process removes acyl substituents from the gellan and lyses the *S. elodea* cells. Solids and cell debris are then removed by acid treatment (to neutralize/acidify the fermentation broth) and filtration to yield a high clarity, low acyl gellan gum. However, this method also results in a gum molecular weight substantially lower than that produced by the native organism, due to depolymerization as well as deacylation. The current commercial method for gellan gum recovery produces gels with a maximum 0.2% gellan gum curdmeter gel strength of about 290 $g/cm^2$ (equivalent to a 0.1% gellan gum curdmeter gel strength of about 113 $g/cm^2$).

SUMMARY OF THE INVENTION

The invention relates to a process for preparing a gellan gum comprising the steps of fermenting *Sphingomonas elodea* in a fermentation broth; optionally clarifying the fermentation broth by a chemical/enzymatic process; mildly deacylating the clarified fermentation broth with a caustic agent; and precipitating the gellan gum from the fermentation broth, wherein the gellan gum has a 0.2% gellan gum curdmeter gel strength of at least about 300 $g/cm^2$, or a 0.1% gellan gum curdmeter gel strength of at least about 117 $g/cm^2$.

In one embodiment of the invention, the *S. elodea* is a PHB-deficient strain. In another embodiment of the invention, the clarification step comprises the steps of heating to a temperature range of from about 30° C. to about 70° C.; treating with one or more antioxidants in combination with one or more chelating agents and a lysozyme enzyme; treating with one or more surfactants; and treating with a protease enzyme.

The invention also relates to gellan gums made by the above methods. In addition, the invention relates to gellan gums having a 0.2% gellan gum curdmeter gel strength of at least about 300 $g/cm^2$, or a 0.1% gellan gum curdmeter gel strength of at least about 117 $g/cm^2$. In one embodiment of the invention, the gellan gum rehydrated in deionized water at a concentration of 1% has a light transmittance of greater than about 60%. In another embodiment of the invention, the gellan gums have a Texture Profile Analysis ("TPA") hardness of at least about 9 pounds (lb.). In yet another embodiment of the invention, the gellan gums have a 1% gellan gum, 90° C. hot viscosity of at least about 25 centipoise (cP).

The invention further relates to food and non-food industrial products comprising the novel gellan gums described herein. In addition, the invention relates to food or non-food industrial products comprising gellan gums prepared by the method described herein. The concentration of high performance gellan gum used in the industrial products of the present invention is from about 20% to about 85% less than the concentration of the currently available commercial product (Kelcogel®) used.

BRIEF DESCRIPTION OF THE DRAWINGS

FIG. 1 is a graph showing the linear correlation between the 0.2% gellan gum curdmeter gel strength test and the 0.1% gellan gum curdmeter gel strength test.

DETAILED DESCRIPTION OF THE INVENTION

The present invention relates to methods for preparing low acyl gellan gums having a greater gel strength than the low acyl gellan gums in the prior art and for preparing partially deacylated gellan gums. The invention also relates to low acyl and partially deacylated gellan gums that have high clarity without the use of a conventional filter press when rehydrated into aqueous solutions. The invention further relates to food and non-food industrial products, such as dessert gels, confectionery, beverages, microbial and tissue culture media, liquid cleaners, and the like, comprising these high performance gellan gums.

High acyl (HA) gellan gums as described in U.S. Pat. No. 5,190,927 have a glycerate content of 11-13% and an acetate content of 4-5%, for a total acyl content of 15-18% (w/w). Low acyl gellan gums, as described herein, are considered to have <1.0% glycerate and <1.0% acetate, or a total acyl content of <2.0%, w/w, on the polymer chain. Partially deacylated gellan gums, as described herein, have the intermediate levels of 1-11% glycerate and 1-4% acetate, for a total acyl content of 2-15%.

*Sphingomonas elodea*, ATCC 31461, mutants derived from this strain, or other suitable strains are grown or fermented aerobically in an aqueous solution known as a fermentation broth by methods known to those of ordinary skill in the art. The media contain sources of carbon, nitrogen, and inorganic salts. In general, carbohydrates (for example glucose, fructose, maltose, sucrose, xylose, mannitol, and the like) can be used either alone or in combination as sources of assimilable carbon in the nutrient medium. In general, the amount of carbohydrate usually varies between about 2% and 4% by weight of the medium. In general, many proteinaceous materials may be used as organic nitrogen sources in the fermentation process. Suitable nitrogen sources include, for example, yeast hydrolysates, soybean meal, cottonseed flour, hydrolysates of casein, corn steep liquor, distiller's solubles, and the like. The sources of nitrogen, either alone or in combination, are used in amounts ranging from about 0.05% to 0.2% by weight of the aqueous medium. Among the inorganic salts which can be incorporated in the culture media are the customary salts capable of providing sodium, potassium, ammonium, calcium, magnesium, phosphate, sulfate, chloride, nitrate, carbonate, and like ions. Also included are trace elements, such as salts of ferrous, zinc, copper, manganese, cobalt, and molybdenum.

Sphingans are secreted as capsular polysaccharides into the fermentation broth. Mutant strains of *S. elodea* having desirable properties may be used. In one embodiment of the invention, a mutant strain of *S. elodea* that is deficient in the production of polyhydroxybutyrate ("PHB"), such as that described in U.S. patent application Ser. No. 11/292,366, filed Dec. 2, 2005, which is incorporated by reference in its entirety, is used. The use of the PHB-deficient strains, along with the clarification process described herein, enables high clarity of reconstituted gellan gums to be achieved for either low acyl gellan gums or partially deacylated gellan gums.

Following fermentation, the sphingans are typically clarified and isolated away from the suspended solids, including the microbial cells and cellular debris that are part of the fermentation broth milieu, by a filtration process to yield clarified sphingans. As described herein, the clarification process may, instead, be a chemical/enzymatic process. Solutions obtained by addition of isolated sphingans to aqueous media and partially purified sphingan solutions may also be clarified using the process of this invention. The aqueous solutions of sphingans containing undesirable fermentation solids useful in the process of this invention may contain about 0.01% to about 10% sphingan by weight of the total weight of the solution. Any aqueous solution containing any of the known sphingans may be used in the practice of this invention.

The high performance low acyl gellan gums of the invention have a greater gel strength than low acyl gellan gums in the prior art. For example, Kelcogel® (CP Kelco, Atlanta, Ga.) products have a maximum 0.2% gellan gum curdmeter gel strength of about 290 g/cm² (equivalent to a 0.1% curdmeter gel strength of about 113 g/cm²), as measured by a Neo Curdmeter® (110 Electric Co., Ltd., Japan). The gel strength of low acyl gellan gums have, in the past, been described using the 0.2% gellan gum curdmeter gel strength test. The upper end of this test procedure is 400 g/cm², which is exceeded by the novel gellan gums of the present invention. Therefore, the gel strength test method has been modified to use 0.1% gellan gum.

The high performance gellan gums of the invention have a 0.2% gellan gum curdmeter gel strength of at least about 300 g/cm², such as at least about 320 g/cm². Equivalently, the high performance gellan gums of the invention have a 0.1% gellan gum curdmeter gel strength of at least about 117 g/cm², such as at least about 125 g/cm², at least about 150 g/cm², at least about 175 g/cm², at least about 200 g/cm², at least about 225 g/cm², at least about 250 g/cm², at least about 275 g/cm², at least about 300 g/cm², and at least about 325 g/cm². Additional embodiments of the present invention may have 0.1% gellan gum curdmeter gel strengths from about 117 g/cm² to about 400 g/cm², such as from about 117 g/cm² to about 156 g/cm² and from about 125 g/cm² to about 250 g/cm².

The high performance low acyl gellan gums of the invention have an increased molecular weight compared to commercially available low acyl gellan gums. While not being bound to a specific theory, the belief is that the high performance low acyl gellan gums of the present invention have novel high gel strength characteristics due to the increase in molecular weight.

In addition, the high performance low acyl and partially deacylated gellan gums of the invention may have high clarity without using a filtration process to remove cells and cell debris. Rehydration and dissolution in water of sphingan clarified by the methods described herein provides a substantially clear sphingan solution. A substantially clear sphingan solution (1% w/w), according to this invention, has a light transmittance greater than about 60%, preferably greater than about 70%, and most preferably greater than about 80%. Light transmittance may be measured at any wavelength in the visible spectrum using conventional techniques and equipment (e.g., commercially available spectrophotometers). The light transmittance is typically measured at wavelengths of about 480 nm to about 680 nm.

Low acyl gellan gums of the present invention have a TPA hardness of at least about 9 lb., such as at least about 15 lb., at least about 20 lb., and at least about 25 lb. Low acyl gellan gums of the present invention also have a 1% gellan gum, 90° C. hot viscosity of at least about 25 cP, such as at least about 75 cP, at least about 175 cP, and at least about 300 cP.

Enzymatic Clarification

In one embodiment of the invention, the aqueous solution of sphingans is clarified by a chemical/enzymatic process comprising treating the sphingan solution in a stepwise manner. The fermentation broth is 1) heated, 2) treated with one or more antioxidants in combination with one or more chelating agents and a lysozyme enzyme, 3) treated with one or more surfactants, 4) treated with a protease enzyme, and 5) optionally treated with a cellulase enzyme.

The first step comprises heating an aqueous sphingan solution to an elevated temperature by conventional techniques, such as temperature control in a jacketed tank, direct steam injection, and the like. Direct steam injection is preferred to minimize heating time. The clarification temperature ranges from about 30° C. to about 70° C., preferably from about 50° C. to about 60° C. The length of time required to heat the sphingan solution to the desired temperature may vary significantly depending upon the size and volume of the sphingan solution to be treated. For example, whereas it may take only several minutes to increase the temperature of a small volume (e.g., 50 ml) of sphingan solution from room temperature to about 60° C., it may take several hours to similarly increase the temperature of 40,000 liters of solution (e.g., as may be present in commercial processing).

The next step comprises treating the aqueous sphingan solution with optionally at least one antioxidant, optionally at least one chelating agent, and at least one lysozyme enzyme. Preferably, the aqueous sphingan solution is treated with at least one antioxidant, at least one chelating agent, and at least one lysozyme enzyme. The antioxidant(s) is typically added in concentration ranges from about 75 parts per million ("ppm") to about 300 ppm, such as from about 150 ppm to about 250 ppm. Typically, the chelating agent(s) is added to the sphingan solution at a concentration ranging from about 150 ppm to about 1000 ppm, such as from about 200 ppm to about 500 ppm. The typical lysozyme concentration ranges from about 25 ppm to about 200 ppm, such as from about 50 ppm to about 150 ppm. The solution is mixed for about 1 hour to about 5 hours, such as about 1.5 hours to about 2.5 hours, and about 1.5 hours to about 2 hours.

The antioxidant may be ascorbic acid, sodium erythorbate, sodium metabisulfite, potassium metabisulfite, potassium bisulfite, sulfur dioxide, butylated hydroxyanisole, cysteine, or sodium sulfite.

Chelating agents that are suitable for use in the process of this invention are compounds or compositions that are capable of sequestering multivalent metal ions (e.g., $Mg^{2+}$, $Ca^{2+}$, $Fe^{2+}$, $Mn^{2+}$, $Cu^{2+}$, etc.) in the sphingan solution by forming poly-dentate complexes with the metal ions and forming a precipitate with the metal ions or adsorbing the metal ions. Examples of useful chelating agents include, but are not limited to, disodium ethylenediamine tetraacetate, dipotassium ethylenediamine tetraacetate, tetrasodium ethylenediamine tetraacetate, tetrapotassium ethylenediamine tetraacetate, citric acid, trisodium citrate, tripotassium citrate, sodium hexametaphosphate, potassium hexametaphosphate, sodium polyphosphate, potassium polyphosphate, sodium pyrophosphate, potassium pyrophosphate, monosodium phosphate, monopotassium phosphate, disodium phosphate, dipotassium phosphate, trisodium phosphate, tripotassium phosphate, sodium bicarbonate, sodium carbonate, potassium carbonate, potassium bicarbonate, a cationic ion exchange resin, ethylenediamine dihydrochloride, ethylenediamine diacetate, ethylenediamine lithium salt, ethylenediamine dihydroiodide, and the like. Preferably, the chelating agents used in the process of this invention include citric acid, and salts of ethylenediamine tetraacetic acid, citric acid, phosphoric acid, pyrophosphoric acid, polyphosphoric acid, carbonic acid, metaphosphoric acid, and ethylenediamine. More preferably, disodium ethylenediamine tetraacetate or citric acid is used as the chelating agent.

The lysozymes suitable for use in this process include the Multifect® lysozyme (Genencor International, Inc., Palo Alto, Calif.) or any lysozyme that may be obtained from a plant, animal, or microbially-derived source.

After treating the sphingan solution with antioxidant(s), chelating agent(s), and lysozyme, the next step is to treat the solution with at least one surfactant. The surfactant(s) is added in a concentration range from about 50 ppm to about 400 ppm, such as from about 150 ppm to about 300 ppm. The solution is then agitated for a period of time of from about 0.5 hours to about 2 hours, such as from about 1 hour to about 1.5 hours.

Surfactants that are suitable for use in the process of this invention are compounds or compositions that are capable of forming aqueous emulsions in the presence of hydrophilic and hydrophobic substances (solids or liquids). Preferably, the surfactants are water or water-alcohol soluble compounds or compositions. Examples of useful surfactants include, but are not limited to, sodium dodecyl sulfate ("SDS"), polyoxyethylenesorbitan monooleate (TWEEN 80 by ICI Americas, Inc., Bridgewater, N.J.), lecithin, monoglycerides, tartaric esters of monoglycerides, phosphated monoglycerides (e.g., as the monosodium salt), lactylated monoglycerides, acetylated monoglycerides, succinylated monoglycerides, ethoxylated monoglycerides, sorbitan esters, polysorbates, polyglycerol esters, sucrose esters, sodium stearoyl lactylate, propylene glycol esters, and the like. More preferably, SDS is used as the surfactant.

The solution is then treated with at least one protease enzyme. The protease enzyme is added in a concentration of about 100 ppm to about 3000 ppm, such as from about 500 ppm to about 2000 ppm, and is mixed with the solution for about 0.5 hours to about 5 hours, such as from about 1 hour to about 4 hours.

The protease enzymes suitable for use in this process may be acid, neutral or alkaline proteases from bacterial, fungal, or plant sources. Exemplary acid protease enzymes useful in the process of this invention include, but are not limited to, proteases produced by microorganisms of the genus *Aspergillus*, such as *A. niger*. The neutral protease enzymes useful in the process of this invention include, but are not limited to, proteases produced by microorganisms, such as *Bacillus amyloliquifaciens*. The alkaline protease enzymes useful in the process of this invention include, but are not limited to, alkaline proteases produced by microorganisms of the genus *Bacillus*, such as *B. subtilis, B. licheniformis*, and *B. pumilis*; proteases elaborated by species of *Streptomyces*, such as *S. fradiae, S. griseus* and *S. rectus*; and proteases obtained from subtilisins, such as subtilisin Novo and subtilisin Carlsberg, including proteases such as subtilopeptidase A and subtilopeptidase B.

Finally, a cellulase enzyme may also be added if the fermentation media contain cellulosic residue. Examples of cellulase enzymes for use in the process of this invention include, but are not limited to, Celluclast® BG (Novozymes A/S, Bagsvaerd, Denmark), Multifect® CL (Genencor International, Inc., Palo Alto, Calif.), Multifect® GC (Genencor International, Inc., Palo Alto, Calif.), and the like.

The enzymes used in the enzymatic treatment step(s) degrade the solid cellular debris to compounds more easily removed during the recovery process, thus improving the purity of the sphingan product and aiding in the clarification process, which improves transmittance of the sphingan product when reconstituted into solution.

It should be noted that the degree of clarification affected by treatment of the sphingan solution with chelating agent(s), antioxidant(s), and surfactant(s), may affect the enzyme concentrations or the time required to complete the subsequent enzyme treatments. For example, increasing the amount of the chelating agent(s), antioxidant(s), and surfactant(s) used in this process may decrease the amount of enzymes used and/or the time required to affect clarification of a sphingan solution.

Deacylation

Either before or after clarification, the gellan gum may then be deacylated with one or more strong or weak caustic agents, such as potassium hydroxide, sodium hydroxide, trisodium phosphate, and the like. Potassium hydroxide is the preferred caustic agent. In one embodiment, the deacylation occurs after clarification by a chemical/enzymatic process. In another embodiment, the deacylation occurs before clarification by a filtration process.

Enough caustic agent is added to increase the pH of the fermentor to a range from about 9.5 to about 12.5, such as from about 9.7 to about 11.7. The broth is then heat treated to a temperature of about 190° F. to about 210° F. After heating, the pH is lowered with an acid solution, such as sulfuric acid, hydrochloric acid, or phosphoric acid, preferably sulfuric acid, to a pH of from about 3.5 to about 9.0, such as from about 4.0 to about 7.0. It should be noted that the extent of deacylation and the properties of the resultant gellan product are affected by the level of alkali treatment. For example, if a strong alkali treatment is used, then the gellan gum will be further deacylated, producing a more firm and brittle gel, and the molecular weight will be reduced, such as in the currently available commercial product. On the other hand, if a milder alkali treatment is used, there will be less of a reduction in molecular weight, and at even milder alkali treatment levels, the gellan gum will have a higher acyl content (i.e. partially deacylated), which will form a more flexible gel.

After deacylation, the gellan gum may be precipitated by methods well-known in the art, such as by the use of isopropyl or ethyl alcohol.

Food and Non-Food Industrial Products

The subject gellan gums are useful as thickeners, e.g. in the food industry, such as beverages, confections, jams and jellies, fabricated foods, water-based gels, pie fillings, dessert gels, icings, dairy products, such as yogurts, puddings, whips, creamers, gelled milks, and ice creams, and the like. Additionally, the subject gelling agents may be used in gelled pet foods, microbial and tissue culture media, liquid cleaners, toothpastes, soap and body washes, deodorant gels, air freshener gels, soft capsules, and other known industrial applications of microbial gels.

The high performance characteristics of the gellan gum described herein enable the gellan gum to provide gelling functionality at lower concentrations than the standard, commercially available low acyl gellan gums. The concentration of gellan gum used is from about 15% to about 90% less, such as about 20% to about 85% less, about 25% to about 75% less, about 30% to about 65% less, and about 35% to about 55% less, than the concentration of the currently available commercial product (Kelcogel®) used. The reduced amount of gellan gum provides cost savings and allows gellan gums to be used economically in other applications where, until now, only lower cost gelling agents, such as agar, could be used.

The high performance gellan gums of the present invention may be used to impart heat stability. In one embodiment, the high performance gellan gums are used in multi-layer dessert gels. The thermally stable gellan gum network helps maintain the shape of the dessert gels with unique designs and patterns during pasteurization at 85° C. The effectiveness of gellan gum in providing the heat stability can be evaluated by visual observation or rheological measurement.

In another embodiment, the gellan gums of the present invention provide heat stability for gummy confections. Heat stability in gummy confections can be evaluated by measuring the increase in diameter of the gummy confection as it becomes deformed and melts.

In yet another embodiment, high performance low acyl gellan gums are used as the main structure component in drinking jellies to provide the characteristic brittle gel network.

Another embodiment of the invention provides for the use of high performance gellan gums in conjunction with other gelling hydrocolloids, such as in water dessert gel systems, to provide a desirable gel texture. The gelling hydrocolloids typically used with gellan gums include, but are not limited to, carrageenan, carrageenan/locust bean gum systems, carrageenan/konjac systems, and xanthan gum/locust bean gum systems.

EXAMPLES

The following examples provide illustrations of the present invention and should not be misconstrued to limit in any way the scope of the present invention.

Example 1

Enzymatic Clarification, Product Recovery, and 0.1% Curdmeter Gel Strength Analysis 4500 L of fermentor broth from the fermentation (Batch No. GB05662) of a PHB-deficient strain of *S. elodea* was heated to a temperature of 50° C. and mixed with mechanical agitation. With continued mixing, 200 ppm of sodium sulfite, 100 ppm Lysozyme, and 250 ppm disodium EDTA were added to the fermentor. The reagents were continuously mixed for two hours while the fermentor temperature was controlled to maintain the elevated temperature. Next, 250 ppm of sodium dodecyl sulfate was added to the fermentor broth and agitated for one hour. Afterward, 1000 ppm of protease enzyme was added to the fermentation broth and mixed with the fermentation broth for 3 hours. Potassium hydroxide was added to the broth to achieve a pH of 11.34 in order to deacylate the polysaccharide.

The broth was recovered by heating to 100° C., adjusting the pH down to 5.59 with sulfuric acid, and precipitating with three volumes of an isopropanol/water azeotropic mixture to one volume of treated fermentation broth. The precipitated fiber was dried in a tray drier and milled to a fine powder. A one gram sample of the dry powder was reconstituted in 950 ml of purified water at ambient temperature. The powder was dispersed by mixing at 600 rpm for about 2 minutes. The beaker containing the sample was placed in a water bath maintained at approximately 100° C. The mixing of the sample was continued until the sample reached 90° C. Stirring was then continued for an additional 10 minutes. 10 ml of 61.6 g/l calcium lactate was then added to the hot sample, and stirred for an additional minute. The sample was then adjusted up to a total solution weight of 1000 g by adding hot purified water. The sample was mixed for an additional minute, and then poured into a jelly cup and stoppered. The sample was then placed in an 8° C. water bath for about two hours.

Gel strength was measured on a Neo Curdmeter®, Model ME-303. For this measurement, a 100 gram spring, an extension rod, a 5.6 mm plunger, and a 100 gram load cell weight were used as described in the Neo Curdmeter® operating manual. For this sample, the 0.1% gram curdmeter gel strength was 317 g/cm$^2$.

Example 2

Enzymatic Clarification, Product Recovery, and Texture Profile Analysis

4500 L of fermentor broth from the fermentation (Batch No. GB05443) of a PHB-deficient strain of *S. elodea* was heated to a temperature of 50° C. and mixed with mechanical agitation. With continued mixing, 200 ppm of sodium sulfite, 100 ppm Lysozyme, and 250 ppm disodium EDTA were added to the fermentor. The reagents were continuously mixed for two hours while the fermentor temperature was controlled to maintain the elevated temperature. Next, 250 ppm of sodium dodecyl sulfate was added to the fermentor broth and agitated for one hour. Afterward, 1000 ppm of protease enzyme was added to the fermentation broth and mixed with the fermentation broth for 3 hours. Potassium hydroxide was added to the broth to achieve a pH of 11.13 in order to deacylate the polysaccharide.

The broth was recovered by heating to 100° C., adjusting the pH down to 5.51 with sulfuric acid, and precipitating with three volumes of an isopropanol/water azeotropic mixture to one volume of treated fermentation broth. The precipitated fiber was dried in a tray drier and milled to a fine powder. A 1.5 gram sample of the dry powder was reconstituted in 305 g deionized water and allowed to mix at ambient temperature with 800 rpm stirring for one minute. The mixture was heated to 90° C., after which the heat source was shut off, and the mixture was stirred for one minute. Next, 3 mL of 0.6 M calcium chloride stock solution was added and stirred for an additional minute. The weight of the mixture was brought up to 301 g with preheated deionized water and stirred again for 30 seconds. The surface air bubbles were removed with a spoon, and the solution was poured into Texture Profile Analysis ("TPA") rings coated with grease, which was held overnight to gel.

The gel was then tested by TPA (Sanderson, G. R. et al., The Texture of Gellan Gum Gels, Gums and Stability for the Food Industry, 4:219-227 (1988)), which is a compression test of free-standing gels. Samples were compressed to 20% of their original height at a rate of 2 inches/minute twice. Modulus, hardness, brittleness and elasticity were measured. The hardness measurement was the maximum force during the first compression cycle and represents the gelling performance (gel strength) of the sample. A TPA hardness of 25.7 lb. was measured.

Example 3

Enzymatic Clarification, Product Recovery, and Hot Viscosity Measurement

4500 L of fermentor broth from the fermentation (Batch No. GB05341) of a PHB-deficient strain of *S. elodea* was heated to a temperature of 50° C. and mixed with mechanical agitation. With continued mixing, 200 ppm of sodium sulfite, 100 ppm Lysozyme, and 250 ppm disodium EDTA were added to the fermentor. The reagents were continuously mixed for two hours while the fermentor temperature was controlled to maintain the elevated temperature. Next, 250 ppm of sodium dodecyl sulfate was added to the fermentor broth and agitated for one hour. Afterward, 1000 ppm of protease enzyme was added to the fermentation broth and mixed with the fermentation broth for 3 hours. Potassium hydroxide was added to the broth to achieve a pH of 11.48 in order to deacylate the polysaccharide.

The broth was recovered by heating to 100° C., adjusting the pH down to 5.4 with sulfuric acid, and precipitating with three volumes of an isopropanol/water azeotropic mixture to one volume of treated fermentation broth. The precipitated fiber was dried in a tray drier and milled to a fine powder. A 3.0 gram sample of the dry powder was slowly reconstituted in a beaker containing 300 mL deionized water, while stirring, in a 90° C. water bath. The hot beaker was weighed on a balance, and the contents of the solution was brought up to 300 grams with deionized water and mixed for 20 seconds. Using a 10 mL syringe, 8 mL of solution was injected into the small sample adapter cup of a Brookfield LV viscometer with a water jacket connected to the hot water bath. Using spindle #18, which was preheated in the water bath, the 1% gellan gum, 90° C. hot viscosity was measured at a viscometer speed of 12 rpm (the rpm was adjusted so that the viscosity measurement was in range). A hot viscosity of 239 cP was measured. The hot viscosity is believed to be related to the molecular weight, and hence gelling performance, of the polysaccharide sample.

Example 4

0.1% Curdmeter Gel Strength Comparison of Kelcogel® and High Performance Gellan Gums A number of 4500 liter *S. elodea* fermentation batches were clarified using the chemical/enzymatic treatment process of Example 1, except the deacylation pH achieved after the potassium hydroxide addition varied from batch to batch. The treated fermentation broth was recovered to dry powder according to the procedure of Example 1. The 0.1% curdmeter gel strength was measured as described in Example 1. The fermentation batch number, deacylation pH, and 0.1% curdmeter gel strength are shown in Table 1, along with three commercially available low acyl gellan gum batches (Kelcogel®) for comparison. The data show that the 0.1% curdmeter gel strengths are significantly higher for the experimental batches.

TABLE 1

Gel Strength Comparison of Kelcogel ® and High Performance Gellan Gums

| Batch/Lot No. | Deacylation pH | 0.1% Curdmeter Gel Strength (g/cm$^2$) |
|---|---|---|
| Kelcogel ® lot 5G3901A | n.a. | 102 |
| Kelcogel ® lot 5G3908A | n.a. | 98.8 |
| Kelcogel ® lot 5G3928A | n.a. | 80.6 |
| GB06623-8 | 11.42 | 351 |
| GB05664-4 | 11.62 | 276 |
| GB05663-1 | 11.0 | 119 |
| GB05255-1 | 10.9 | 142 |
| GB05341-6 | 11.06 | 157 |
| GB04555-1 | 11.35 | 340 |

Example 5

Texture Profile Analysis of Kelcogel® and High Performance Gellan Gums

A number of 4500 liter *S. elodea* fermentation batches were clarified using the chemical/enzymatic treatment process of Example 1, except the deacylation pH achieved after the potassium hydroxide addition varied from batch to batch The treated fermentation broth was recovered to dry powder according to the procedure of Example 1. The Texture Profile Analysis ("TPA") was measured as described in Example 2. The fermentation batch number, deacylation pH, and TPA harness (lb.) are shown in Table 2, along with three commercially available low acyl gellan gum batches (Kelcogel®) for comparison. The data show that the TPA hardness values are significantly higher for the experimental batches.

TABLE 2

TPA Comparison of Kelcogel ® and High Performance Gellan Gums

| Batch/Lot No. | Deacylation pH | TPA Hardness (lb.) |
|---|---|---|
| Kelcogel ® lot 5G3901A | n.a. | 7.9 |
| Kelcogel ® lot 5G3908A | n.a. | 7.5 |
| Kelcogel ® lot 5G3928A | n.a. | 7.5 |
| GB06623-8 | 11.42 | 23.3 |
| GB05664-1 | 11.27 | 36.1 |
| GB06405-1 | 10.52 | 25.5 |
| GB06602-4 | n.a. | 11.9 |
| GB05663-7 | 11.63 | 14.9 |
| GB05443-4 | 11.6 | 19.8 |

Example 6

Hot Viscosity Measurement Comparison of Kelcogel® and High Performance Gellan Gums A number of 4500 liter *S. elodea* fermentation batches were clarified using the chemical/enzymatic treatment process of Example 1, except the deacylation pH achieved after the potassium hydroxide addition varied from batch to batch The treated fermentation broth was recovered to dry powder according to the procedure of Example 1. The hot viscosity was measured as described in Example 3. The fermentation batch number, deacylation pH, and hot viscosity (centipoise) are shown in Table 3, along with three commercially available low acyl gellan gum batches (Kelcogel®) for comparison. The data show that the 1% gellan gum, 90° C. hot viscosity values are significantly higher for the experimental batches.

TABLE 3

Hot Viscosity Comparison of Kelcogel ® and High Performance Gellan Gums

| Batch/Lot No. | Deacylation pH | Hot Viscosity (cP) |
|---|---|---|
| Kelcogel ® lot 5G3901A | n.a. | 11.1 |
| Kelcogel ® lot 5G3908A | n.a. | 6.7 |
| Kelcogel ® lot 5G3928A | n.a. | 19.2 |
| GB06623-8 | 11.42 | 178 |
| GB05664-1 | 11.27 | 836 |
| GB06405-1 | 10.52 | 380 |
| GB05663-8 | 11.63 | 45.6 |
| GB05662-6 | 11.34 | 194 |
| GB04555-11 | 11.74 | 25.5 |

Example 7

Effect of Deacylation pH on 0.1% Curdmeter Gel Strength

A number of 4500 liter *S. elodea* fermentation batches were clarified using the chemical/enzymatic treatment process of Example 1, except that the deacylation pH was varied during the recovery of the batch by modifying the potassium hydroxide addition levels. After deacylation, the treated, deacylated fermentation broth was recovered to dry powder according to the procedure of Example 1. The 0.1% curdmeter gel strength was measured as described in Example 1. The fermentation batch number, deacylation pH, and 0.1% curdmeter gel strength are shown Table 4. The data show that typically a higher curdmeter gel strength is achieved as the deacylation pH is lowered.

TABLE 4

Correlation Between Deacylation pH and Gel Strength

| Batch/Lot No. | Deacylation pH | 0.1% Curdmeter Gel Strength (g/cm$^2$) |
|---|---|---|
| GB06622 | 10.0 | 323 |
|  | 10.2 | 310 |
|  | 11.19 | 259 |
| GB06610 | 11.38 | 325 |
|  | 11.4 | 316 |
|  | 11.54 | 301 |
| GB04555 | 11.35 | 340 |
|  | 11.74 | 186 |
| GB06612 | 10.2 | 339 |
|  | 11.27 | 316 |
|  | 11.8 | 294 |

Example 8

Effect of Deacylation pH on TPA Hardness and Hot Viscosity

A number of 4500 liter *S. elodea* fermentation batches were clarified using the chemical/enzymatic treatment process of Example 1, except that the deacylation pH was varied during the recovery of the batch by modifying the potassium hydroxide addition levels. After deacylation, the treated, deacylated fermentation broth was recovered to dry powder according to the procedure of Example 1. The TPA hardness and hot viscosity were measured as described in Examples 2 and 3, respectively. The fermentation batch number, deacylation pH, TPA hardness, and hot viscosity are shown in Table 5. The data show that typically higher TPA hardness values and 1% gellan gum, 90° C. hot viscosities are achieved as the deacylation pH is lowered.

TABLE 5

Correlation Between Deacylation pH and TPA Hardness and Hot Viscosities

| Batch/Lot No. | Deacylation pH | TPA Hardness (lb.) | Hot Viscosity (cP) |
|---|---|---|---|
| GB06405 | 10.14 | 20.3 | 97 |
|  | 11.05 | 17.5 | 54.7 |
|  | 11.28 | 14.2 | 42.5 |
| GB05443 | 11.13 | 25.7 | 320 |
|  | 11.33 | 23.4 | 162 |
|  | 11.48 | 21.7 | 95.1 |
|  | 11.60 | 19.8 | 76.8 |
| GB05664 | 11.27 | 36.1 | 836 |
|  | 11.37 | 28.5 | 460 |
|  | 11.57 | 25.6 | 188 |
|  | 11.62 | 24.5 | 140 |

TABLE 5-continued

Correlation Between Deacylation pH and TPA Hardness and Hot Viscosities

| Batch/Lot No. | Deacylation pH | TPA Hardness (lb.) | Hot Viscosity (cP) |
|---|---|---|---|
| GB04552 | 11.2 | 19.7 | 121 |
|  | 11.6 | 10.8 | 19.7 |

Example 9

Relative Molecular Weight Measurements by Gel Permeation Chromatography/Multiple Angle Laser Light Scattering ("GPC/MALLS")

Dilute aqueous stock solutions of commercially available Kelcogel® and the high performance gellan gums of the present invention were prepared by dissolving 0.20 gram of the gellan sample in 200 ml of deionized water along with 0.01 gram of ethylenediaminetetra-acetic acid ("EDTA"). The solutions were heated to 50° C., cooled, and then diluted to the chosen concentration (0.033 to 0.050% gellan) in 25 mM tetramethyl ammonium chloride, which was previously filtered through a 0.2 micron filter.

The GPC/MALLS system consisted of a Waters 600 controller, a Waters 610 HPLC pump, a Waters 717+autosampler, a series of two GPC columns (a 30 cm Waters Ultrahydrogel 2000 column and a 30 cm Waters Ultrahydrogel Linear column), a DAWN DSP laser photometer (Wyatt Technology Corp., Santa Barbara, Calif.), and a Waters 410 differential refractometer (all Waters products from Waters Corp., Milford, Mass.). Next, 0.10 mL of the samples were injected into the eluent flow (25 mM tetramethylammonium chloride at 0.50 ml/min) and were separated based on molecular size by the size exclusion chromatography columns. As the sample eluted from the column, the relative molecular weight and concentration profiles were determined by the light scattering and refractive index detectors. An index of refraction increment (dn/dc) of 0.145 was used to determine the sample concentration (and relative molecular weight) as a function of elution volume. This value was chosen based on values reported in the literature (see Paoletti et al., Carbohydrate Polymers, 15:171 (1991)) and what is typical for polysaccharides in aqueous salt solutions.

The relative weight-average ("Mw") and number-average ("Mn") molecular weights were calculated using a linear extrapolation of light scattering detectors #8-16. The weight-average and number-average molecular weights of the three commercial Kelcogel® gellan gum samples were averaged to provide the control relative molecular weight, which was assigned a value of 1.0. This provided normalized values for comparing the experimental batches with the commercial product. The relative molecular weight results are given in Table 6. The results show that, by this methodology, the commercially available Kelcogel® samples have significantly lower molecular weights than the samples of the high performance low acyl gellan gums of the present invention. The data indicate that the average Mw of the high performance low acyl gellan gum samples was 1.83 times the average of the control, commercially available low acyl gellan gum samples.

TABLE 6

Relative Molecular Weights Measurements by GPC/MALLS

| Batch/Lot No. | Mw | Mn |
|---|---|---|
| Kelcogel ® lot 5G3901A | 0.93 | 0.96 |
| Kelcogel ® lot 5G3908A | 1.08 | 1.11 |
| Kelcogel ® lot 5G3928A | 0.99 | 0.93 |
| GB05810-3 | 1.67 | 2.00 |
| GB05811-1 | 1.35 | 1.48 |
| GB05341-6 | 2.42 | 3.04 |
| GB05341-10 | 1.96 | 2.43 |
| GD05619-1 | 1.75 | 2.05 |
| GD05620-1 | 1.82 | 2.29 |

Example 10

Relative Molecular Weight Measurements by Atomic Force Microscopy ("AFM")

0.1% gellan gum solutions were prepared by hydrating 0.1 g of gellan in 100 mL of deionized water and heating to 50° C. These stock solutions were diluted further with deionized water for AFM measurements. Aliquots of the 0.1% gellan solutions were withdrawn using a 10 μL pipette and diluted with either 10 mL or 20 mL of deionized water. 25 μL of these dilute gellan solutions (0.5 ppm and 1.0 ppm) were sprayed onto freshly cleaved mica surfaces and dried in a vacuum oven at approximately 50° C. for 30 minutes.

The dried samples were imaged using a Nanoscope® IIIa (Veeco Instruments Inc., Woodbury, N.Y.). A 200 μL "J" stage was used in the Tapping Mode (intermittent contact mode) with a tapping mode etched silica ("TESP") tip. A series of at least ten 5 μL×5 μL scans were collected for each sample at various locations throughout the mica surface. Gellan chain contour lengths were measured for each sample by using at least two representative 5 μL×5 μL scan images. The contour lengths of roughly 200 molecules were measured for each sample to generate relative molecular weight averages and distributions.

Two commercially available Kelcogel® samples (Lot Nos. 5G3908A and 5G3928A) and one sample of the high performance gellan gum of the present invention (Batch No. GB05810-3) were analyzed for molecular weight by AFM. The contour lengths of the two commercial Kelcogel® gellan gum samples were averaged to provide the control relative molecular weight, which was assigned a value of 1.0. This provided normalized values for comparing the experimental batches with the commercial product. The relative molecular weight results are given in Table 7. Column "n" refers to the number of molecules used to measure contour length. The AFM results serve as a second, independent molecular weight technique that supports the GPC/MALLS results, confirming that the novel high performance low acyl gellan gum of the present invention has a significantly higher molecular weight than commercially available low acyl gellan gum.

TABLE 7

Relative Molecular Weight Analysis of Gellan Gums by AFM

| Batch/Lot No. | Type | Mw | Mn | n |
|---|---|---|---|---|
| 5G3908A | Kelcogel ® | 1.20 | 1.17 | 191 |
| 5G3928A | Kelcogel ® | 0.80 | 0.83 | 216 |
| GB05810-3 | high performance gellan gum | 1.99 | 1.58 | 190 |

Example 11

Clarity and Acyl Content of High Performance Low Acyl Gellan Gums

A number of 4500 liter fermentation batches of a PHB-deficient strain of S. elodea were clarified using the chemical/enzymatic treatment process of Example 1. The fermentation broth was deacylated with potassium hydroxide and then recovered to dry powder according to the procedure of Example 1. To measure clarity, 3 g of dry powder was reconstituted to a concentration of 1% in deionized water according to the procedure in Example 3. The hot, reconstituted gel was poured into a tube, and the percent transmittance was measured on a spectrophotometer at a wavelength of 490 nm. The percent transmittance is shown in Table 8.

To measure the acyl content, 1.5 g of dry powder was vortexed for 15 seconds with 15 g of 60% isopropyl alcohol ("IPA"). After vortexing, the liquid was removed by centrifuging at 5000 rpm for 10 minutes and decanting. This was repeated five times with 60% IPA to remove unbound organic acid salts and finally, with 15 g of 99% IPA to facilitate drying of the sample. After the final decanting, the sample was recovered from the centrifuge tube and dried overnight in a vacuum oven at 50° C. Next, 25 mg of dry powder was reconstituted in 5 mL deionizer water at 80° C. The sample was then hydrolyzed in 0.5 M trifluoroacetic acid ("TFA") overnight at 100° C. The hydrolyzed sample was diluted to 25 mL and filtered through a 0.45 µL nylon disk-type syringe filter. The organic acids in the filtrate were quantified using a Dionex Corporation's (Sunnyvale, Calif.) HPLC system equipped with an IonPac® ICE-ASI ion-exclusion column and a conductivity detector. The percent acyl content is shown in Table 8.

TABLE 8

Clarity and Acyl Content of High Performance Low Acyl Gellan Gums

| Batch/Lot No. | % Transmittance | % Glycerate | % Acetate | Total % Acyl |
|---|---|---|---|---|
| GB05811-1 | 92.0 | 0.00 | 0.03 | 0.03 |
| GB05810-1 | 91.6 | 0.03 | 0.04 | 0.07 |
| GB05624-1 | 82.8 | 0.02 | 0.04 | 0.06 |
| GB06623-1 | 88.7 | 0.19 | 0.05 | 0.24 |
| GB06622-1 | 87.5 | 0.07 | 0.01 | 0.08 |
| GB06611-1 | 66.4 | 0.30 | 0.07 | 0.37 |
| GB06610-1 | 88.4 | 0.32 | 0.03 | 0.35 |
| GB06405-1 | 82.0 | 0.23 | 0.09 | 0.32 |
| GB06602-1 | 85.5 | 0.07 | 0.06 | 0.13 |
| GB05443-1 | 88.9 | 0.10 | 0.10 | 0.20 |
| GB05664-1 | 89.1 | 0.58 | 0.08 | 0.66 |
| GB05663-4 | 92.5 | 0.03 | 0.11 | 0.14 |
| GB05255-6 | 88.6 | 0.02 | 0.10 | 0.12 |
| GB05341-74 | 93.0 | 0.51 | 0.20 | 0.71 |

Example 12

Clarity and Acyl Content of High Performance Partially Deacylated Gellan Gums

Two 4500 liter fermentation batches of S. elodea (using a low PHB-producing mutant) were clarified using the chemical/enzymatic treatment process of Example 1. The fermentation broth was mildly deacylated with potassium hydroxide and then recovered to dry powder according to the procedure of Example 1 (Batch No. GB05341 was deacylated at two different pH conditions). The dry powder was reconstituted to a concentration of 1% in deionized water according to the procedure in Example 3. The hot reconstituted gellan gum solution was poured into a tube, and the percent transmittance was measured on a spectrophotometer at a wavelength of 490 nm. A sample of dry powder was also reconstituted in deionized water, hydrolyzed in 0.5 M TFA at a temperature of 100° C. for 18 hours, and the glycerate and acetate constituents of the hydrolyzed gum were measured by HPLC. The deacylation pH, percent transmittance, and percent acyl content are shown in Table 9.

TABLE 9

Clarity and Acyl Contents of High Performance Partially Deacylated Gellan Gums

| Batch/Lot No. | Deacylation pH | % Transmittance | % Glycerate | % Acetate | Total % Acyl |
|---|---|---|---|---|---|
| GB05662-1 | 10.91 | 68.6 | 1.07 | 1.60 | 2.67 |
| GB05341-1 | 10.55 | 84.9 | 5.32 | 2.70 | 8.02 |
| GB05341-3 | 10.69 | 92.8 | 2.92 | 2.21 | 5.13 |

Example 13

Use of High Performance Low Acyl Gellan Gum to Improve Heat Stability of Dessert Gels During Pasteurization The relative effectiveness of three high performance low acyl gellan gum samples (Batch Nos. GB06612-8, GB06405-5, and GB06622-6) and one commercial Kelcogel® sample (Lot No. 5G3928A) in providing heat stability to a dessert gel system (see formulation in Table 10) was compared using a Bohlin CVO Rheometer (Malvern Instruments Ltd., Worcestershire, United Kingdom). The elastic modulus ("G") of a hot dessert gel solution was measured using the rheometer with a 4-cm 4° cone and plate geometry at 0.15 strain and 1 Hz as it was being cooled from 80° C. to 20° C. at 5° C./min. The G' of the gel was then measured while it was being reheated from 20° C. to 90° C. at 5° C./min. A minimum G' of 5 Pa during the reheating phase was previously determined to be necessary for the dessert gel system to maintain its integrity during a commercial pasteurization process (85° C. for 30 min). Each gellan gum sample was tested at three different concentrations between 0.0125% and 0.025%, and the minimum G' during reheating of each sample was plotted as a function of gellan concentration. The plot was then used to determine the gellan concentration required to achieve a G' of 5 Pa using interpolation. The relative effectiveness in providing heat stability, as expressed as the concentration required to achieve a G' of 5 Pa, for each sample tested is shown in Table 11. The results indicated that the three high performance gellan gums, on average, required about 24% less than the amount of Kelcogel® to provide similar heat stability to the dessert gel system.

TABLE 10

Dessert Gel Formulation for Heat Stability Evaluation

| Ingredients | % |
| --- | --- |
| Gellan gum | Varies from 0.0125-0.025 |
| Carrageenan | 0.24 |
| Locust bean gum | 0.08 |
| Konjac powder | 0.16 |
| Sugar | 20 |
| KCl | 0.1 |
| 0.3 M $CaCl_2$ solution | 2 |
| 1.2 M pH 3.9 citrate buffer | 1 |
| DI water | To 100 |

TABLE 11

Relative Effectiveness of Gellan Gum Samples in Providing Heat Stability to a Dessert Gel System

| Batch/Lot No. | Concentration required to achieve a G' of 5 Pa (%) |
| --- | --- |
| Kelcogel® 5G3928A | 0.0198 |
| GB06612-8 | 0.0152 |
| GB06405-5 | 0.0159 |
| GB06622-6 | 0.0143 |

Example 14

Use of High Performance Low Acyl Gellan Gum in Drinking Jellies

A high performance gellan gum sample (Batch No. GB06623-7) was used at concentrations between 0.06% and 0.1% in a drinking jelly and compared to a control made with 0.1% of a commercial Kelcogel® sample (Lot No. 5G3928A). The formulation shown in Table 12 was prepared by combining the gellan gum and sodium citrate and adding the combined mixture to DI water under agitation. Then, the mixture was heated to 90° C. Next, the remaining ingredients were added and mixed for 1 minute at 90° C. Afterward, the mixture was adjusted for water loss due to evaporation with hot DI water. Aluminum-lined plastic drinking jelly bags were filled with hot solution and heated sealed. Finally, the jelly bags were pasteurized in an 85° C. water bath for 30 minutes and then cooled to room temperature with cold running tap water.

TABLE 12

Drinking Jelly Formulation

| Ingredients | % |
| --- | --- |
| White Grape Juice Conc. (56° Brix) | 25.3 |
| Sodium citrate | 0.3 |
| Citric acid | 0.25 |
| Calcium Lactate | 0.05 |
| Gellan gum | Varies from 0.06-0.1 |
| DI water | To 100 |

The drinking jelly was evaluated for syneresis (% water separated from gel) and gel texture (by a three-member taste panel) after 1 week of storage at room temperature. Based on the syneresis and sensory evaluation results shown in Table 13, a sample having a high performance gellan gum concentration between 0.06% and 0.07% would give a similar drinking jelly to the control made with 0.1% Kelcogel®. Therefore, much less of the high performance gellan gum would be needed compared to the currently available gellan gum.

TABLE 13

Syneresis and Sensory Evaluation of Water Drinking Jelly

| Sample | Syneresis (%) | Sensory evaluation of gel texture |
| --- | --- | --- |
| 0.1% Kelcogel® | 4.36 | Control jelly |
| 0.1% GB06623-7 | 2.31 | Stronger gel than 0.1% Kelcogel® |
| 0.09% GB06623-7 | 3.91 | Stronger gel than 0.1% Kelcogel® |
| 0.08% GB06623-7 | 3.72 | Stronger gel than 0.1% Kelcogel® |
| 0.07% GB06623-7 | 3.28 | Slightly stronger gel than 0.1% Kelcogel® |
| 0.06% GB06623-7 | 8.64 | Weaker gel than 0.1% Kelcogel® |

Example 15

Use of High Performance Low Acyl Gellan Gum in a Confectionery Jelly

A commercially available Kelcogel® sample (Lot No. 5G3901A) and a sample of the high performance low acyl gellan gum of the present invention (Batch No. GB06405-5) were compared in a typical confectionery jelly formulation, which is shown in Table 14. The formulation was prepared by boiling corn syrup, high fructose corn syrup, and water (A) in a kettle. Sugar, gellan gum, and phosphates (B) were dry blended and then dispersed into the kettle while mixing. The mixture was brought to a boil while mixing and then boiled for 2 to 3 minutes to ensure gum hydration. Sugar (C) was added gradually to avoid cooling the batch and was dissolved by boiling. The mixture was then reduced to 79% refractometer soluble solids while mixing. Next, acid and citrate solutions (D) were combined (flavor and color could have also been added if desired) while mixing. Finally, the mixture was immediately deposited into prepared starch molds and held at 30° C.-35° C. (86° F.-95° F.) for 2 to 3 days until 82%-83% refractometer soluble solids was reached.

TABLE 14

Confectionery Jelly Formulation

| Order of Addition | Ingredients | % by Weight | Grams |
| --- | --- | --- | --- |
| A | Corn syrup, 43DE, 81% solids | 33.00 | 165.00 |
| | High fructose corn syrup, 42% fructose, 71% solids | 10.00 | 50.00 |
| | Water | 30.00 | 150.00 |
| B | Sugar, fine granular | 8.00 | 40.00 |
| | Gellan Gum | 0.80 | 4.00 |
| | Dicalcium phosphate, anhydrous | 0.10 | 0.50 |
| | Sodium hexametaphosphate | 0.03 | 0.15 |
| C | Sugar, fine granular | 35.00 | 175.00 |
| D | Citric acid, monohydrate; 50% sol'n w/w | 1.00 | 5.00 |
| | Sodium citrate, dihydrate; 33% sol'n w/w | 0.75 | 3.75 |
| | Total: | 118.68 | 593.40 |
| | Evaporation: | −18.68 | −93.40 |
| | Yield: | 100.00 | 500.00 |

Four trials were conducted: one control at 0.8% Kelcogel® and three with high performance gellan gums at concentration levels at 0.8%, 0.6%, and 0.4%). Samples were starch-molded in the shape of discs with a 25 mm diameter and a 10 mm height. Finished samples were tested for TPA hardness at 70% compression. Reported values are the average TPA hardness of 5 samples per trial, plus or minus one standard deviation, and are shown in Table 15.

TABLE 15

TPA Evaluation of Confectionery Jelly

| Trial | Gellan Gum ID | Concentration (%) | TPA Hardness (lb.) |
|---|---|---|---|
| 1 | Kelcogel ® 5G3901A | 0.8 | 40.6 ± 2.4 |
| 2 | GB06405-5 | 0.8 | 94.5 ± 1.7 |
| 3 | GB06405-5 | 0.6 | 72.6 ± 1.8 |
| 4 | GB06405-5 | 0.4 | 41.4 ± 1.5 |

At the control concentration (0.8%), high performance gellan gum produced an average TPA hardness value 233% higher than that of Kelcogel® gellan gum. Furthermore, high performance gellan gum at a concentration of 0.4% achieves a TPA hardness equivalent to that of the control concentration (0.8%) of Kelcogel® gellan gum. This indicates that Kelcogel® gellan gum can be replaced with about 50% less of the high performance gellan gum in confectionery jellies.

Example 16

Use of High Performance Low Acyl Gellan Gum to Provide Heat Stability in a Gummy Confection A commercially available Kelcogel® sample (Lot No. 6A5307A) and a sample of the high performance gellan gum of the present invention (Batch No. GB06622-8) were compared in a gummy confectionery formulation shown in Table 16. The formulation was prepared by first making a gelatin presolution of water and gelatin (A) and then holding the solution at 60° C. (140° F.) for 3-4 hours to dissolve. Meanwhile, corn syrup, water, and sodium citrate solution (B) were boiled in a kettle. Then, sugar and gellan gum (C) were dry blended and dispersed into the kettle while mixing. The mixture was brought to a boil while mixing and boiled 2 to 3 minutes to ensure gum hydration. Next, sugar (D) was gradually added to avoid cooling the batch and dissolved by boiling. The mixture was then reduced to 85%-86% refractometer soluble solids while mixing. Afterward, the gelatin presolution (A) was added and mixed well. Then, the acid (E) with flavor and color (as desired) was added while mixing. The mixture was about 77% refractometer soluble solids. Finally, the mixture was deposited immediately into prepared starch molds and held at 25° C.-30° C. (77° F.-86° F.) for 2 to 3 days until 81%-82% refractometer soluble solids was reached.

TABLE 16

Gummy Confectionery Formulation

| Order of Addition | Ingredients | % by Weight | Grams |
|---|---|---|---|
| A | Water | 9.00 | 45.00 |
|  | Gelatin, 250 bloom type A | 6.00 | 30.00 |
| B | Corn syrup, 63DE, 82% solids | 40.50 | 202.50 |
|  | Water | 33.00 | 165.00 |
| C | Sugar, fine granular | 2.00 | 10.00 |
|  | Gellan Gum | 0.24 | 1.20 |
|  | Sodium hexametaphosphate | 0.03 | 0.15 |
| D | Sugar, fine granular | 35.00 | 175.00 |
| E | Citric acid, monohydrate; 50% sol'n w/w | 1.25 | 6.25 |
|  | Calcium chloride, anhydrous; 5% sol'n w/w | 1.00 | 5.00 |
|  | Total: | 128.02 | 640.10 |
|  | Evaporation: | −28.02 | −140.10 |
|  | Yield: | 100.00 | 500.00 |

Five trials were conducted: one with no gellan gum (the "gelatin control"), two with Kelcogel® (0.24% and 0.12%), and two with high performance gellan gum (0.12% and 0.06%). Samples were starch-molded in the shape of discs with a 25 mm diameter and a 10 mm height. Individual finished samples were packaged in vapor impermeable oriented polypropylene heat-sealed bags and tested for heat stability in a laboratory oven at 45° C. As the samples deformed and melted at this elevated temperature, their diameter increased. After 8 hours, the average diameters of the samples were measured, and the increase in the average diameters of the samples calculated. The measurements are shown in Table 17.

TABLE 17

Heat Stability Evaluation of Gummy Confections

| Trial | ID | Starting Average Diameter (mm) | Final Average Diameter (mm) | Average Diameter Increase (%) |
|---|---|---|---|---|
| 1 | Gelatin control (0% gellan gum) | 25 | 38 | 52 |
| 2 | w/ 0.24% Kelcogel ® 6A5307A | 25 | 27.5 | 10 |
| 3 | w/ 0.12% Kelcogel ® 6A5307A | 25 | 31.5 | 26 |
| 4 | w/ 0.12% GB06622-8 | 25 | 25.5 | 2 |
| 5 | w/ 0.06% GB06622-8 | 25 | 27.5 | 10 |

Compared with the gelatin control, gellan gum of either type and at any concentration evaluated reduced the amount of average diameter increase significantly; however, an average diameter increase of 10% was judged through observation to be the maximum allowable level to consider the sample acceptably heat stable. A 0.24% Kelcogel® sample achieved adequate heat stability (i.e., an average diameter increase of ≦10%). High performance gellan gum, by comparison, achieved adequate heat stability at a concentration of only 0.06%. By this heat stability measure, Kelcogel® can be replaced with high performance gellan gum at a concentration about 75% lower in gummy confections.

Example 17

Use of High Performance Low Acyl Gellan Gum as a Texture Modifier in Water Dessert Gels Two dessert gels are made: Gel A comprises Kelcogel® and Gel B comprises high performance low acyl gellan gum, both further comprise xanthan gum and locust bean gum. The dessert gel formulations are provided in Table 18. Although Gel A has a greater amount of gellan gum than Gel B, both Gel A and Gel B have very similar gel textures and eating qualities. Thus, it takes less of the high performance low acyl gellan gum to provide the same effect as the Kelcogel® gellan gum.

TABLE 18

Comparison of Water Dessert Gels Containing Kelcogel ® or High Performance Low Acyl Gellan Gum

| Ingredients | Gel A (% Concentration) | Gel B (% Concentration) |
|---|---|---|
| Kelcogel ® | 0.1 | — |
| High performance gellan gum | — | 0.065 |
| Xanthan gum | 0.07 | 0.07 |
| Locust bean gum | 0.07 | 0.07 |
| Sucrose | 18 | 18 |
| Orange Juice | 10 | 10 |
| Sodium citrate dihydrate | 0.15 | 0.15 |

TABLE 18-continued

Comparison of Water Dessert Gels Containing Kelcogel ®
or High Performance Low Acyl Gellan Gum

| Ingredients | Gel A (% Concentration) | Gel B (% Concentration) |
| --- | --- | --- |
| Citric acid (anhydrous) | 0.25 | 0.25 |
| Water | 71.36 | 71.395 |

While the present invention is described above with respect to what is currently considered to be its preferred embodiments, it is to be understood that the invention is not limited to that described above. To the contrary, the invention is intended to cover various modifications and equivalent arrangements included within the spirit and scope of the appended claims.

What is claimed is:

1. A process for preparing a low acyl gellan gum comprising the steps of:
   a. fermenting a PHB-deficient strain of *Sphingomonas elodea* in a fermentation broth;
   b. clarifying the fermentation broth by a chemical/enzymatic process comprising the steps of:
      i. heating the fermentation broth to a temperature from about 30° C. to about 70° C.;
      ii. treating the fermentation broth with one or more antioxidants in combination with one or more chelating agents and a lysozyme enzyme;
      iii. treating the fermentation broth of step ii with one or more surfactants; and
      iv. treating the fermentation broth of step iii with a protease enzyme to obtain a clarified fermentation broth;
   c. deacylating the clarified fermentation broth with a caustic agent to obtain a gellan gum having a total acyl content of 2.0% or less; and
   d. precipitating the gellan gum from the fermentation broth;
   wherein the precipitated gellan gum has a 0.2% gellan gum curdmeter gel strength of at least about 300 g/cm$^2$.

2. The process of claim 1, wherein the precipitated gellan gum has a 0.2% gellan gum curdmeter gel strength of at least about 325 g/cm$^2$.

3. The process of claim 1, wherein the precipitated gellan gum has a 0.1% gellan gum curdmeter gel strength of at least about 117 g/cm$^2$.

4. The process of claim 1, wherein the precipitated gellan gum has a 0.1% gellan gum curdmeter gel strength of at least about 125 g/cm$^2$.

5. The process of claim 1, wherein the precipitated gellan gum has a 0.1% gellan gum curdmeter gel strength of at least about 150 g/cm$^2$.

6. The process of claim 1, wherein the precipitated gellan gum has a 0.1% gellan gum curdmeter gel strength of at least about 175 g/cm$^2$.

7. The process of claim 1, wherein the precipitated gellan gum has a 0.1% gellan gum curdmeter gel strength of at least about 200 g/cm$^2$.

8. The process of claim 1, wherein the precipitated gellan gum has a 0.1% gellan gum curdmeter gel strength of at least about 225 g/cm$^2$.

9. The process of claim 1, wherein the precipitated gellan gum has a 0.1% gellan gum curdmeter gel strength of at least about 250 g/cm$^2$.

10. The process of claim 1, wherein the precipitated gellan gum has a 0.1% gellan gum curdmeter gel strength of at least about 275 g/cm$^2$.

11. The process of claim 1, wherein the precipitated gellan gum has a 0.1% gellan gum curdmeter gel strength of at least about 300 g/cm$^2$.

12. The process of claim 1, wherein the precipitated gellan gum has a 0.1% gellan gum curdmeter gel strength of at least about 325 g/cm$^2$.

13. The process of claim 1, wherein the precipitated gellan gum has a 0.1% gellan gum curdmeter gel strength from about 117 g/cm$^2$ to about 400 g/cm$^2$.

14. The process of claim 1, wherein the precipitated gellan gum has a 0.1% gellan gum curdmeter gel strength from about 117 g/cm$^2$ to about 156 g/cm$^2$.

15. The process of claim 1, wherein the precipitated gellan gum has a 0.1% gellan gum curdmeter gel strength from about 125 g/cm$^2$ to about 250 g/cm$^2$.

16. The process of claim 1, wherein the antioxidant is sodium sulfite.

17. The process of claim 1, wherein the chelating agent is selected from the group consisting of disodium ethylenediamine tetraacetate, dipotassium ethylenediamine tetraacetate, tetrasodium ethylenediamine tetraacetate, tetrapotassium ethylenediamine tetraacetate, citric acid, trisodium citrate, tripotassium citrate, sodium hexametaphosphate, potassium hexametaphosphate, sodium polyphosphate, potassium polyphosphate, sodium pyrophosphate, potassium pyrophosphate, monosodium phosphate, monopotassium phosphate, disodium phosphate, dipotassium phosphate, trisodium phosphate, tripotassium phosphate, sodium bicarbonate, sodium carbonate, potassium carbonate, potassium bicarbonate, a cationic ion exchange resin, ethylenediamine dihydrochloride, ethylenediamine diacetate, ethylenediamine lithium salt, and ethylenediamine dihydroiodide.

18. The process of claim 1, wherein the chelating agent is disodium ethylenediamine tetraacetate.

19. The process of claim 1, wherein the chelating agent is citric acid.

20. The process of claim 1, wherein the surfactant is selected from the group consisting of sodium dodecyl sulfate, polyoxyethylenesorbitan monooleate, lecithin, monoglycerides, tartaric esters of monoglycerides, phosphated monoglycerides, lactylated monoglycerides, acetylated monoglycerides, succinylated monoglycerides, ethoxylated monoglycerides, sorbitan esters, polysorbates, polyglycerol esters, sucrose esters, sodium stearoyl lactylate, and propylene glycol esters.

21. The process of claim 1, wherein the surfactant is sodium dodecyl sulfate.

22. The process of claim 1, wherein the caustic agent is selected from the group consisting of potassium hydroxide, sodium hydroxide, and trisodium phosphate.

23. The process of claim 1, wherein the caustic agent is potassium hydroxide.

24. A gellan gum prepared by the process of claim 1.

25. The gellan gum of claim 24, wherein the gellan gum has a 0.2% gellan gum curdmeter gel strength of at least about 325 g/cm$^2$.

26. The gellan gum of claim 24, wherein the gellan gum has a 0.1% gellan gum curdmeter gel strength of at least about 117 g/cm$^2$.

27. The gellan gum of claim 24, wherein the gellan gum has a 0.1% gellan gum curdmeter gel strength of at least about 125 g/cm$^2$.

28. The gellan gum of claim 24, wherein the gellan gum has a 0.1% gellan gum curdmeter gel strength of at least about 150 g/cm$^2$.

29. The gellan gum of claim 24, wherein the gellan gum has a 0.1% gellan gum curdmeter gel strength of at least about 175 g/cm$^2$.

30. The gellan gum of claim 24, wherein the gellan gum has a 0.1% gellan gum curdmeter gel strength of at least about 200 g/cm$^2$.

31. The gellan gum of claim 24, wherein the gellan gum has a 0.1% gellan gum curdmeter gel strength of at least about 225 g/cm$^2$.

32. The gellan gum of claim 24, wherein the gellan gum has a 0.1% gellan gum curdmeter gel strength of a at least about 250 g/cm$^2$.

33. The gellan gum of claim 24, wherein the gellan gum has a 0.1% gellan gum curdmeter gel strength of at least about 275 g/cm$^2$.

34. The gellan gum of claim 24, wherein the gellan gum has a 0.1% gellan gum curdmeter gel strength of at least about 300 g/cm$^2$.

35. The gellan gum of claim 24, wherein the gellan gum has a 0.1% gellan gum curdmeter gel strength of at least about 325 g/cm$^2$.

36. The gellan gum of claim 24, wherein the gellan gum has a 0.1% gellan gum curdmeter gel strength from about 117 g/cm$^2$ to about 400 g/cm$^2$.

37. The gellan gum of claim 24, wherein the gellan gum has a 0.1% gellan gum curdmeter gel strength from about 117 g/cm$^2$ to about 156 g/cm$^2$.

38. The gellan gum of claim 24, wherein the gellan gum has a 0.1% gellan gum curdmeter gel strength from about 125 g/cm$^2$ to about 250 g/cm$^2$.

39. A gellan gum comprising a total acyl content of less than 2.0%, wherein the gellan gum has a 0.2% gellan gum curdmeter gel strength of at least about 300 g/cm$^2$.

40. A gellan gum comprising a total acyl content of 2.0% or less, wherein the gellan gum has a 0.1% gellan gum curdmeter gel strength of at least about 117 g/cm$^2$.

41. An industrial product comprising the gellan gum of claim 24.

42. The industrial product of claim 41, wherein the product is selected from the group consisting of beverages, confections, jams and jellies, fabricated foods, water-based gels, pie fillings, dessert gels, icings, yogurts, puddings, whips, creamers, gelled milks, and ice creams.

43. The industrial product of claim 41, wherein the product is selected from the group consisting of gelled pet foods, microbial and tissue culture media, liquid cleaners, toothpastes, soaps and body washes, deodorant gels, air freshener gels, and soft capsules.

44. The industrial product of claim 41, wherein the gellan gum is used in a concentration from about 15% to about 90% less than a concentration of a currently available commercial low acyl gellan gum used in the industrial product.

45. The industrial product of claim 41, wherein the gellan gum is used in a concentration from about 20% to about 85% less than a concentration of a currently available commercial low acyl gellan gum used in the industrial product.

46. The industrial product of claim 41, wherein the gellan gum is used in a concentration from about 25% to about 75% less than a concentration of a currently available commercial low acyl gellan gum used in the industrial product.

47. The industrial product of claim 41, wherein the gellan gum is used in a concentration from about 30% to about 65% less than a concentration of a currently available commercial low acyl gellan gum used in the industrial product.

48. The industrial product of claim 41, wherein the gellan gum is used in a concentration from about 35% to about 55% less than a concentration of a currently available commercial low acyl gellan gum used in the industrial product.

49. The industrial product of claim 41, wherein the gellan gum is used in conjunction with at least one gelling hydrocolloid selected from the group consisting of carrageenan, locust bean gum, konjac, and xantham gum.

50. A process for preparing a low acyl gellan gum comprising the steps of:
   a. fermenting a PHB-deficient strain of *Sphingomonas elodea* in a fermentation broth;
   b. deacylating the fermentation broth with a caustic agent to obtain a gellan gum having a total acyl content of 2.0% or less;
   c. clarifying the fermentation broth by filtration; and
   d. precipitating the gellan gum from the clarified fermentation broth;
   wherein the gellan gum has a 0.1% gellan gum curdmeter gel strength of at least about 117 g/cm$^2$.

* * * * *